United States Patent [19]

Inman

[11] Patent Number: 5,612,301
[45] Date of Patent: Mar. 18, 1997

[54] HAIR CONDITIONING SHAMPOO COMPOSITIONS WITH SILICONE CONDITIONING AGENT

[75] Inventor: Everett J. Inman, Cincinnati, Ohio

[73] Assignee: The Procter & Gamble Company, Cincinnati, Ohio

[21] Appl. No.: 385,224

[22] Filed: Feb. 8, 1995

Related U.S. Application Data

[63] Continuation of Ser. No. 185,105, Jan. 21, 1994, abandoned, which is a continuation of Ser. No. 8,257, Jan. 25, 1993, abandoned, which is a continuation of Ser. No. 681,016, Apr. 5, 1991, abandoned.

[51] Int. Cl.$^6$ .............. C11D 1/82; C11D 1/72; C11D 1/12
[52] U.S. Cl. .............. 510/122; 510/123; 510/125; 510/127; 510/466; 424/70.19; 424/70.21; 424/70.24; 424/70.31; 424/70.11
[58] Field of Search .............. 252/174.15, DIG. 13, 252/174.21, 174.22, 174.17; 424/70.11, 70.31, 70.19, 70.24; 510/122, 123, 125, 127, 466

[56] References Cited

U.S. PATENT DOCUMENTS

| | | | |
|---|---|---|---|
| 2,826,551 | 3/1958 | Geen | 252/89 |
| 3,964,500 | 6/1976 | Drakoff | 132/7 |
| 4,343,726 | 8/1982 | Egan | 252/547 |
| 4,364,837 | 12/1982 | Pader | 252/173 |
| 4,741,855 | 5/1988 | Grote et al. | 252/142 |
| 4,788,006 | 11/1988 | Bolich et al. | 252/550 |
| 5,000,868 | 3/1991 | Wittpenn et al. | 252/106 |
| 5,034,218 | 7/1991 | Duvel | 424/70 |
| 5,151,210 | 9/1992 | Steuri et al. | 252/174.17 |

FOREIGN PATENT DOCUMENTS

| | | |
|---|---|---|
| 80104605 | 2/1981 | European Pat. Off. . |
| 0024301 | 7/1981 | European Pat. Off. . |
| 0153435 | 9/1985 | European Pat. Off. . |
| 54-44039 | 4/1979 | Japan . |
| 849433 | 9/1960 | United Kingdom . |

OTHER PUBLICATIONS

McCutcheon's Emulsifiers and Detergents 1990, North American Edition (McCutcheon Div., Inc. Publishing Co., Glen Rock, NJ) p. 200.

*Primary Examiner*—Christine Skane
*Assistant Examiner*—Kery A. Fries
*Attorney, Agent, or Firm*—Leonard W. Lewis; Anthony D. Sabatelli; David K. Dabbiere

[57] ABSTRACT

Disclosed are hair conditioning shampoo compositions, containing a detersive surfactant component, a silicone hair conditioning agent, and water and preferably comprising a suspending agent for the silicone conditioning agent. The detersive surfactant component comprises, at least in part, polyethylene glycol glyceryl fatty ester nonionic surfactant. The compositions hereof provide improved silicone deposition.

11 Claims, No Drawings

HAIR CONDITIONING SHAMPOO COMPOSITIONS WITH SILICONE CONDITIONING AGENT

This is a continuation of application Ser. No. 08/185,105, filed on Jan. 21, 1994, now abandoned, which is a continuation of application Ser. No. 08/008,257, filed on Jan. 25, 1993, now abandoned, which is a continuation of application Ser. No. 07/681,016, filed on Apr. 5, 1991 now abandoned.

TECHNICAL FIELD

The present invention is related to hair conditioning shampoo compositions having dispersed, non-volatile silicone conditioning agents, including hair rinse compositions and hair-conditioning shampoo compositions.

BACKGROUND OF THE INVENTION

Human hair becomes soiled due to its contact with the surrounding atmosphere and, to a greater extent, from sebum secreted by the head. The build-up of sebum causes the hair to have a dirty feel and an unattractive appearance. The soiling of the hair necessitates it being shampooed with frequent regularity.

Shampooing the hair cleans by removing excess soil and sebum. However, the shampooing process has disadvantages in that the hair can be left in a wet, tangled and generally unmanageable state. Shampooing can also result in the hair becoming dry or "frizzy" due to the removal of natural oils or other hair moisturizing materials. After shampooing, the hair can also suffer from a perceived loss of "softness". Softness, of course, is a generally desirable attribute for many users of shampoo products. A variety of approaches have been developed to alleviate the after-shampoo problems. These range from the inclusion of hair conditioning aids in shampoos to post-shampoo application of hair conditioners, i.e., hair rinses. Hair rinses typically work by depositing a polymeric film, cationic hair conditioning surfactant, or other material onto the hair. However, such solutions to a very prevalent problem have not been fully satisfactory. For one thing, hair rinses are generally liquid in nature and must be applied in a separate step following the shampooing, left on the hair for a length of time, and rinsed with fresh water. This, of course, is time consuming and is not convenient.

While a wide variety of shampoos have been disclosed which contain conditioning aids, conventional executions of these have not been totally satisfactory for a variety of reasons. A prevalent problem relates to compatibility problems between good cleaning anionic surfactants and the conventional cationic agents which are good conditioning agents.

Silicones are materials which can provide excellent hair conditioning benefits and which are not incompatible with anionic detersive surfactants.

Silicones in shampoo compositions have been disclosed in a number of different publications. Such publications include U.S. Pat. No. 2,826,551, Geen, issued Mar. 11, 1958; U.S. Pat. No. 3,964,500, Drakoff, issued Jun. 22, 1976; U.S. Pat. No. 4,364,837, Pader, issued Dec. 21, 1982; and British Patent 849,433, Woolston, issued Sep. 28, 1960. While these patents disclose silicone containing compositions, they did not provide answers to all of the problems encountered in making a satisfactory product. One problem is that of keeping a dispersed, insoluble silicone material suspended and the total product stable. Recently, stable silicone-containing hair conditioning shampoos have been described in U.S. Pat. No. 4,741,855, Grote and Russell, issued May 3, 1988, which discloses shampoo with cleaning surfactant, an insoluble, non-volatile silicone, water, and a suspending agent such as long chain esters of ethylene glycol, esters of long chain fatty acids, long chain amine oxides, etc. Stable silicone-containing hair conditioning shampoos have also been disclosed in U.S. Pat. No. 4,788,066, Bolich and Williams, issued Nov. 29, 1988, which discloses a xanthan gum suspending agent.

Stable, silicone-containing hair conditioning shampoos have recently attained substantial success in the marketplace. These shampoos can provide excellent hair conditioning benefits to the user. However, it would be desirable to improve these types of shampoos by increasing the efficiency of the silicone hair conditioner incorporated into such shampoo in order to reduce the amount of silicone that is incorporated into the shampoo and, consequently, to reduce raw materials cost. One factor affecting effectiveness of the silicone hair conditioner is the ability of the silicone to deposit upon the hair.

It is an object of this invention to specifically provide silicone hair conditioner-containing shampoo compositions characterized by improved silicone hair conditioner deposition upon the hair.

Unless otherwise indicated, all percentages are calculated by weight of the total composition and all ratios are calculated on a weight basis.

SUMMARY OF THE INVENTION

The present invention provides silicone hair conditioning shampoo compositions having improved silicone hair conditioner deposition upon the hair. The compositions of the present invention comprise a detersive surfactant, a dispersed insoluble, nonvolatile silicone hair conditioning agent, and water. The detersive surfactant component includes a combination of anionic surfactant and a polyethylene glycol glyceryl fatty ester nonionic surfactant, and optionally contains amphoteric, zwitterionic, or other nonionic surfactants, or mixtures thereof. The silicone conditioning agent is typically suspended in the composition with a suspending aid. Surprisingly, the polyethylene glycol glyceryl fatty ester, hereinafter PEG glyceryl fatty ester, can improve the deposition of the silicone hair conditioning agent upon the hair.

More particularly, the present invention provides a shampoo composition comprising:

(a) from about 5% to about 50% of a detersive surfactant component, said detersive surfactant component comprising from about 0.5% to about 20%, by weight of the composition, of polyethylene glycol glyceryl fatty ester nonionic surfactant;

(b) from about 0.01% to about 10% of a dispersed, nonvolatile, insoluble silicone hair conditioning agent;

(c) water.

Typically, the compositions hereof will comprise a suspending agent to maintain the silicone stably dispersed in the composition.

The invention, including preferred embodiments thereof, is described in more detail in the Detailed Description of the Invention, which follows.

DETAILED DESCRIPTION OF THE INVENTION

The essential as well as certain preferred and optimal components of the compositions of the present invention are described below.

Detersive Surfactant

The shampoo compositions of the present invention comprise a detersive surfactant to provide cleaning performance to the composition.

The detersive surfactant will generally total from about 5% to about 50%, preferably from about 8% to about 30%, more preferably from about 10% to about 25%, of the composition. The detersive surfactant component will be selected from anionic, nonionic, cationic, zwitterionic and amphoteric surfactants. Preferably, the compositions hereof contain at least about 2% anionic surfactant, preferably from about 5% to about 20%. Cationic surfactants, typically included for hair conditioning benefits or to assist in formation of a gel-like rheology in combination with, e.g., fatty materials, if used, should not significantly interfere with the effectiveness of anionic surfactants included for detersive purposes.

Polyethylene Glycol Glyceryl Fatty Ester Nonionic Surfactant

The detersive surfactant component hereof will comprise a polyethylene glycol glyceryl fatty ester nonionic surfactant as an essential component. The polyethylene glycol glyceryl fatty esters, i.e., PEG glyceryl fatty esters hereof will generally have a degree of polymerization of from about 5 to about 200, and the fatty ester of the surfactant will have an aliphatic hydrocarbyl radical of from about 8 to 20 carbons. More particularly, the PEG glyceryl fatty esters will generally be of the formula:

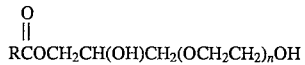

wherein n is from about 5 to about 200, preferably from about 20 to about 100, more preferably from about 30 to about 85, and RC(O)— is an ester wherein R comprises an aliphatic radical having from about 7 to 19 carbon atoms, preferably from about 9 to 17 carbon atoms, more preferably from about 11 to 17 carbon atoms, most preferably from about 11 to 14 carbon atoms.

Suitable glyceryl fatty ester portions of these surfactants include glyceryl cocoate, glyceryl tallowate, glyceryl palmate, glyceryl stearate, glyceryl laurate, glyceryl oleate, glyceryl ricinoleate, and glyceryl fatty esters derived from triglycerides, such as palm oil, almond oil, and corn oil.

Preferred glyceryl esters include glyceryl tallowate and glyceryl cocoate.

Suitable surfactants of this class are commercially available from Sherex Chemical Co. (Dublin, Ohio, U.S.A.) under their Varonic® LI line of surfactants. These include, for example, Varonic LI 48 (polyethylene glycol (n=80) glyceryl tallowate, alternately referred to as PEG 80 glyceryl tallowate), Varonic LI 2 (PEG 28 glyceryl tallowate), Varonic LI 420 (PEG 200 glyceryl tallowate), and Varonic LI 63 and 67 (PEG 30 and PEG 80 glyceryl cocoates), and from Croda, Inc. (New York, N.Y., U.S.A.) under their Crovol® line of materials, such as Crovol A-40 (PEG 20 almond glyceride, Crovol A-70 (PEG 60 almond glyceride), Crovol M-40 (PEG 20 maize glyceride), Crovol M-70 (PEG 60 maize glyceride), Crovol PK-40 (PEG 12 palm kernel glyceride), and Crovol PK-70 (PEG-45 palm kernel glyceride). Especially preferred are monotallowate and cocoate fatty ester derivatives of polyethylene glycol, or mixtures thereof, particularly materials such as PEG 82 glyceryl monotallowate and PEG 30 glyceryl cocoate, and mixtures thereof.

The PEG glyceryl fatty ester nonionic surfactants will typically be utilized at levels of from about 0.5% to about 20%, by weight, of the composition, preferably from about 5% to about 15%, more preferably from about 7% to about 11%.

The PEG glyceryl fatty esters will preferably be used in combination with other surfactants, preferably with anionic surfactants and combinations of anionic surfactants and amphoteric and/or zwitterionic surfactants. Other nonionic surfactants can also be used.

Anionic Surfactants

Anionic detersive surfactants useful herein include alkyl and alkyl ether sulfates. These materials have the respective formulae $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having from about 8 to about 24 carbon atoms. Preferably, R has from about 12 to about 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with about 1 to about 10, and especially about 3, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the present invention are sodium and/or ammonium salts of coconut alkyl triethylene glycol ether sulfate, tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 4 moles of ethylene oxide. Such a mixture also comprises from about 0 to about 20% by weight $C_{12-13}$ compounds; from about 60 to about 100% by weight of $C_{14-15-16}$ compounds, from about 0 to about 20% by weight of $C_{17-18-19}$ compounds; from about 3 to about 30% by weight of compounds having a degree of ethoxylation of 0; from about 45 to about 90% by weight of compounds having a degree of ethoxylation of from about 1 to about 4; from about 10 to about 25% by weight of compounds having a degree of ethoxylation of from about 4 to about 8; and from about 0.1 to about 15% by weight of compounds having a degree of ethoxylation greater than about 8.

Another suitable class of anionic surfactants are the water-soluble salts of the organic, sulfuric acid reaction products of the general formula:

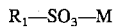

wherein $R_1$ is chosen from the group consisting of a straight or branched chain, saturated aliphatic hydrocarbon radical having from about 8 to about 24, preferably about 12 to about 18, carbon atoms; and M is a cation. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{12-18}$ n-paraffins.

Additional examples of anionic surfactants which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other anionic synthetic surfactants of this variety are set forth in U.S. Pat. Nos. 2,486,921; 2,486,922; and 2,396,278.

Still other anionic surfactants include the class designated as succinamates. This class includes such surface active agents as disodium N-octadecylsulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Other suitable anionic surfactants utilizable herein are olefin sulfonates having about 12 to about 24 carbon atoms. The term "olefin sulfonates" is used herein to mean compounds which can be produced by the sulfonation of α-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The α-olefins from which the olefin sulfonates are derived are mono-olefins having about 12 to about 24 carbon atoms, preferably about 14 to about 16 carbon atoms. Preferably, they are straight chain olefins. Examples of suitable 1-olefins include 1-dodecene; 1-tetradecene; 1-hexadecene; 1-octadecene; 1-eicosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific α-olefin sulfonate mixture of the above type is described more fully in the U.S. Pat. No. 3,332,880, Pflaumer and Kessler, issued Jul. 25, 1967, incorporated herein by reference.

Another class of anionic surfactants are the β-alkyloxy alkane sulfonates. These compounds have the following formula:

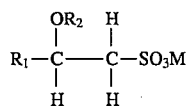

where $R_1$ is a straight chain alkyl group having from about 6 to about 20 carbon atoms, $R_2$ is a lower alkyl group having from about 1 (preferred) to about 3 carbon atoms, and M is a water-soluble cation as hereinbefore described.

Specific examples of β-alkyloxy-alkane-1-sulfonates, or alternatively 2-alkyloxy-alkane-1-sulfonates, having low hardness (calcium ion) sensitivity useful herein include: potassium-β-methoxydecanesulfonate, sodium 2-methoxytridecanesulfonate, potassium 2-ethoxytetradecylsulfonate, sodium 2-isopropoxyhexadecylsulfonate, lithium 2-t-butoxytetradecyl-sulfonate, sodium β-methoxyoctadecylsulfonate, and ammonium β-n-propoxydodecylsulfonate.

Many additional synthetic anionic surfactants are described in *McCutcheon's, Emulsifiers and Detergents,* 1989 *Annual*, published by M. C. Publishing Co., which is incorporated herein by reference. Also U.S. Pat. No. 3,929,678, Laughlin et al., issued Dec. 30, 1975, discloses many other anionic as well as other surfactant types and is incorporated herein by reference. Soaps, of course, also fall within the scope of anionic detersive surfactants that can be used.

Nonionic Surfactants

Nonionic surfactants in addition to the PEG glyceryl fatty esters can be used as detersive surfactants. They are preferably used in combination with an anionic, amphoteric, or zwitterionic surfactant, or mixtures thereof. Nonionic surfactants include those broadly defined as compounds produced by the condensation of alkylene oxide groups (hydrophilic in nature) with an organic hydrophobic compound, which may be aliphatic or alkyl aromatic in nature. Examples of classes of nonionic surfactants are:

1. The polyethylene oxide condensates of alkyl phenols, e.g., the condensation products of alkyl phenols having an alkyl group containing from about 6 to about 20 carbon atoms, preferably from about 6 to about 12, in either a straight chain or branched chain configuration, with ethylene oxide, the said ethylene oxide being present in amounts equal to from about 10 to about 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of about 2,500 to about 3,000, are satisfactory.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

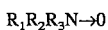

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

$$RR'R''P \rightarrow O$$

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R'' are each alkyl or monohydroxyalkyl groups containing from about 1 to about 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide. 3,6,9,-trioxaoctadecyldimethylphosphine oxide, cetyldimethylphosphine oxide, 3-dodecoxy-2-hydroxypropyldi(2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleydimethylphosphine oxide, 2-hydroxydodecyldimethylphosphine oxide.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include: octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

7. Other nonionic surfactants can also be used in the compositions hereof. Polysorbates, e.g., sucrose esters of fatty acids. Such materials are described in U.S. Pat. No. 3,480,616, e.g., sucrose cocoate (a mixture of sucrose esters of a coconut acid, consisting primarily of monoesters, and sold under the tradenames GRILLOTEN LSE 87K from RITA, and CRODESTA SL-40 from Croda).

Alkyl polysaccharide nonionic surfactants are disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group. The polysaccharide can contain from about 1.0 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

Optionally, and less desirably, there can be a polyalkyleneoxide chain joining the hydrophobic moiety and the polysaccharide moiety. The preferred alkyleneoxide is ethylene oxide. Typical hydrophobic groups include alkyl groups, either saturated or unsaturated, branched or unbranched containing from about 8 to about 18, preferably from about 10 to about 16, carbon atoms. Preferably, the alkyl group is a straight chain saturated alkyl group. The alkyl group can contain up to about 3 hydroxy groups and/or the polyalkyleneoxide chain can contain up to about 10, preferably less than 5, alkylene moieties. Suitable alkyl polysaccharides are octyl, nonyldecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/or galactoses. Suitable mixtures include coconut alkyl, di-, tri-, tetra-, and pentagluscosides and tallow alkyl, tetra-, penta-, and hexaglucosides.

The preferred alkyl polysaccharides are alkylpolyglycosides of the formula $$R^2O(C_nH_{2n}O)(glycosyl)_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 2 or 3, preferably 2; t is from 0 to about 10, preferably 0; and x is from 1.3 to about 10, preferably from 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

$$\overset{(R^3)x}{\underset{|}{R^2-Y(+)-CH_2-R^4Z(-)}}$$

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxy-propane-1-phosphate;
3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Other zwitterionics such as betaines can also be useful in the present invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention. Preferred betaines for use in the present compositions are cocoamidopropyl betaine, cocobetaine, lauryl amidopropyl betaine, and oleyl betaine.

Examples of amphoteric surfactants which can be used in the compositions of the present invention are those which are broadly described as derivatives of al iphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspattic acids such as those produced according to the teaching of U.S. Pat. No. 2,438,091, and the products sold under the trade name "Miranol" and described in U.S. Pat. No. 2,528,378.

Other amphoteric surfactants include sultaines and amidosultaines. Sultaines and amidosultaines can advantageously be utilized as foam enhancing surfactants that are mild to the eye in partial replacement of anionic surfactants. Sultaines, including amidosultaines, include for example, cocodimethylpropylsultaine, stearyldimethylpropylsultaine, lauryl-bis-(2-hydroxyethyl) propylsultaine and the like; and the amidosultaines such as cocoamidodimethylpropyl sultaine, stearyl amidododimethylpropylsultaine, laurylamidobis-(2-hydroxyethyl) propylsultaine, and the like. Preferred are amidohydroxysultaines such as the $C_{12}$–$C_{18}$ hydrocarbyl amidopropyl hydroxysultaines, especially $C_{12}$–$C_{14}$ hydrocarbyl amido propyl hydroxysultaines, e.g., laurylamidopropyl hydroxysultaine and cocamidopropyl hydroxysultaine. Other sultaines are disclosed in U.S. Pat. No. 3,950,417, issued Apr. 13, 1976, incorporated herein by reference.

Other specific amphoterics include imidazolinium materials depicted by Formula I:

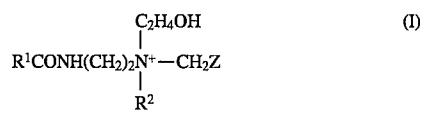

wherein $R^1$ is $C_8$–$C_{22}$ alkyl or alkenyl, $R^2$ is hydrogen, $CO_2M$, $CH_2CO_2M$, or $CH_2CH_2M$, Z is $CO_2M$ or $CH_2CO_2M$, and M is hydrogen, alkali metal, alkaline earth metal, ammonium or alkanol ammonium.

Suitable materials of this type are marketed under the tradename MIRANOL and are understood to comprise a complex mixture of species. The CTFA Cosmetic Dictionary, Third Edition, indicates Formula I as the formula for these materials. Traditionally, the Miranols have been described as having the following cyclic structure:

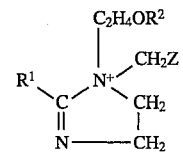

wherein $R^1$, $R^2$, and Z are defined as above, and M is hydrogen, alkali metal, alkaline earth metal, ammonium or alkanol ammonium. In practice, a complex mixture of species is likely to exist and hereinafter Formula I is intended to cover mixtures of species as defined above.

Materials included are cocoamphocarboxypropionate, cocoamphocarboxy propionic acid, and cocoamphocarboxyglycinate. Mixtures of these materials may also be used. The most preferred material of this type for use in the present invention is cocoamphocarboxyglycinate (also known as cocoamphodiacetate).

Specific commercial products providing the imidazolinium derivative component of the present compositions include those sold under the trade names of MIRANOL C2M CONC. N.P., MIRANOL C2M CONC. O.P., MIRANOL C2M SF, MIRANOL CM SPECIAL (Miranol, Inc.); ALKATERIC 2CIB (Alkaril Chemicals); AMPHOTERGE W-2 (Lonza, Inc.); MONATERIC CDX-38, MONATERIC CSH-32 (Mona Industries); REWOTERIC AM-2C (Rewo Chemical Group); and SCHERCOTIC MS-2 (Scher Chemicals).

Another specific class of amphoteric surfactants is defined by the aminoalkanoates of Formula II:

and the iminodialkanoates of Formula III:

and mixtures thereof; wherein n and m are numbers from 1 to 4, R is $C_8$–$C_{22}$ alkyl or alkenyl, and M is hydrogen, alkali metal, alkaline earth metal, ammonium or alkanolammonium.

Examples of amphoteric surfactants falling within Formula II include n-alkylamino-propionates and n-alkyl iminodipropionates. Such materials are sold under the tradename DERIPHAT by Henkel and MIRATAINE by Miranol, Inc. Specific examples include N-lauryl-beta-amino propionic acid or salts thereof, and N-lauryl-beta-imino-dipropionic acid (DERIPHAT 160C) or salts thereof, and mixtures thereof.

The preferred shampoos contain from about 2% to about 16% of alkyl sulfates and from 0% to about 14% of ethoxylated alkyl sulfates in combination with the essential PEG glyceryl fatty esters. The preferred embodiments also preferably comprise from about 0.5% to about 10%, preferably from about 1% to about 8% amphoteric or zwitterionic surfactants, or a mixture thereof.

Silicone Conditioning Agent

An essential component of the present invention is a nonvolatile, insoluble silicone conditioning agent. The shampoo compositions, in particular, will generally comprise from about 0.01% to about 10%, by weight, of the silicone conditioning agent, preferably from about 0.05% to about 5%, more preferably from about 0.05% to about 3%, most preferably from about 0.1% to about 2.5%. The silicone conditioning agent comprises a nonvolatile, insoluble silicone fluid. The silicone conditioning agent for use herein in shampoo compositions will preferably have average viscosity of from about 1,000 to about 2,000,000 centistokes at 25° C., more preferably from about 10,000 to about 1,800,000 centistokes, even more preferably from about 100,000 to about 1,500,000 centistokes. Lower viscosity nonvolatile silicone conditioning agents, however, can also be used. Viscosity can be measured by means of a glass capillary viscometer as set forth in Dow Corning Corporate Test Method CTM0004, Jul. 20, 1970.

As used hereinafter, the term "insoluble" in reference to the silicone conditioning agent shall mean that the silicone material is not soluble in water. The term "nonvolatile" in reference to the silicone conditioning agent as used herein shall be interpreted according to the meaning well understood to those skilled in the art, i.e., the silicone fluid exhibits very low or no significant vapor pressure at ambient conditions. The term "silicone fluid" shall mean flowable silicone materials having a viscosity of less than 1,000,000 centistokes at 25° C. Generally, the viscosity of the fluid will be between about 5 and 1,000,000 centistokes at 25° C., preferably between about 10 and about 100,000 centistokes. The silicone conditioning agent hereof can also comprise silicone gums, which are also nonvolatile and insoluble. Silicone gums are later described. The term "silicone", as used herein, shall be synonomous with the term "polysiloxane".

Suitable nonvolatile silicone fluids for use in hair conditioning agents include polyalkyl siloxanes, polyaryl siloxanes, polyalkylaryl siloxanes, polyether siloxane copolymer and mixtures thereof. However, other silicone fluids having hair conditioning properties may be used. The nonvolatile polyalkyl siloxane fluids that may be used include, for example, polydimethylsiloxanes. These siloxanes are available, for example, from the General Electric Company as a Viscasil series and from Dow Corning as the Dow Corning 200 series. Preferably, the viscosity ranges from about 10 centistokes to about 100,000 centistokes at 25° C.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymer that may be used includes, for example, a polypropylene oxide modified dimethylpolysiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

Silicone fluids hereof also include polyalkyl or polyaryl siloxanes with the following structure:

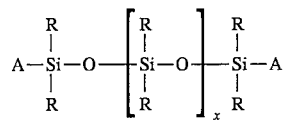

wherein R is alkyl or aryl, and x is an integer from about 7 to about 8,000 may be used. "A" represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

References disclosing suitable silicone fluids include U.S. Pat. No. 2,826,551, Geen; U.S. Pat. No. 3,964,500, Drakoff, issued Jun. 22, 1976; U.S. Pat. No. 4,364,837, Pader; and British Patent 849,433, Woolston. All of these patents are incorporated herein by reference. Also incorporated herein by reference is *Silicon Compounds* distributed by Petrarch Systems, Inc., 1984. This reference provides an extensive (though not exclusive) listing of suitable silicone fluids.

Another silicone fluid that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, *Chemistry and Technology of Silicones*, New York: Academic Press 1968. Also describing silicone gums are General Electric Silicone Rubber Product Data Sheets SE 30, SE 33, SE 54 and SE 76. All of these described references are incorporated herein by reference. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

Preferably the silicone hair conditioning agent comprises a mixture of a polydimethylsiloxane gum, having a viscosity, at 25° C., greater than about 1,000,000 centistokes and polydimethylsiloxane fluid having a viscosity, at 25° C., of from about 10 centipoise to about 100,000 centistokes, wherein the ratio of gum to fluid is from about 30:70 to about 70:30, preferably from about 40:60 to about 60:40.

Cationic silicone fluids and gums may be used, although nonionic silicone fluids and gums are preferred.

Water

Water is the last essential component of the present invention. It is generally present at a level of from about 20% to about 95%, preferably from about 50% to about 85%, more preferably from about 60% to about 85%, by weight of the composition.

Suspending Agent

Any suspending agent useful for suspending the silicone hair conditioning agent in dispersed form in the shampoo compositions hereof is preferably used. A suspending agent is particularly important in pourable liquid formulations.

The preferred suspending agents in the present compositions are long chain acyl derivative materials, long chain amine oxides, or mixtures of such materials wherein such suspending agents are present in the composition in crystalline form. These suspending agents are described in U.S. Pat. No. 4,741,855, Grote and Russell, issued May 3, 1988, incorporated herein by reference. Included are ethylene glycol esters of fatty acids preferably having from about 16 to about 22 carbon atoms. More preferred are the ethylene glycol stearates, both mono and distearate, but particularly the distearate containing less than about 7% of the mono stearate. Other suspending agents found useful are alkanol amides of fatty acids, preferably having from about 16 to about 22 carbon atoms, more preferably about 16 to 18 carbon atoms. Preferred alkanol amides are stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having $C_8$–$C_{22}$ chains may be used.

Suspending agents also include long chain amine oxides such as alkyl ($C_{16}$–$C_{22}$)dimethyl amine oxides, e.g., stearyl dimethyl amine oxide. If the compositions contain an amine oxide or a long chain acyl derivative which is a surfactant, the suspending function could also be provided by such amine oxide or surfactant and additional suspending agent may not be needed.

Other long chain acyl derivatives that can be used include N,N-dihydrocarbyl amido benzoic acid and soluble salts thereof (e.g., Na and K salts), particularly N,N-di(hydrogenated) $C_{16}$, $C_{18}$ and tallow amido benzoic acid species of this family, which are commercially available from Stepan Company (Northfield, Ill., U.S.A.).

The acyl derivative and amine oxide suspending agents are typically present in pourable, liquid formulations at a level of from about 0.1% to about 5.0%, preferably from about 0.5% to about 3.0%. The suspending agent serves to assist in suspending the silicone material and may give pearlescence to the product. Mixtures of suspending agents are also suitable for use in the compositions of this invention.

Another type of suspending agent that can be used is xanthan gum. Shampoo compositions utilizing xanthan gum as a suspending agent for the silicone hair conditioning component are described in U.S. Pat. No. 4,788,006, Bolich and Williams, issued Nov. 29, 1988, incorporated herein by reference. Xanthan gum is biosynthetic gum material that is commercially available. It is a heteropolysaccharide with a molecular weight of greater than 1 million. It is believed to contain D-glucose, D-mannose and D-glucuronate in the molar ratio of 2.8:2.0:2.0. the polysaccharide is partially acetylated with 4.7% acetyl. This information and other is found in Whistler, Roy L. Editor *Industrial Gums—Polysaccharides and Theft Derivatives* New York: Academic Press, 1973. Kelco, a Division of Merck & Co., Inc. offers xanthan gum as Keltrol®. The gum, when used as the silicone hair conditioning component suspending agent, will typically be present in pourable, liquid formulations at a level of from about 0.3% to about 3%, preferably from about 0.4% to about 1.2% in the compositions of the present invention.

Combinations of long chain acyl derivatives and xanthan gum are disclosed as a suspending agent for silicone hair conditioners in U.S. Pat. No. 4,704,272, Oh et al., issued Nov. 3, 1987, incorporated herein by reference, and may also be used in the present compositions.

Another type of suspending agent that can be used is carboxyvinyl polymer. Preferred polymers are copolymers of acrylic acid crosslinked with polyallylsucrose as described in U.S. Pat. No. 2,798,053, Brown, issued Jul. 2, 1957, incorporated herein by reference. These polymers are provided by B. F. Goodrich Company as, for example, Carbopol 934, 940, 941, and 956.

A carboxyvinyl polymer is an interpolymer of a monomeric mixture comprising a monomeric olefinically unsaturated carboxylic acid, and from about 0.1% to about 10% by weight of the total monomers of a polyether of a polyhydric alcohol, which polyhydric alcohol contains at least four carbon atoms to which are attached at least three hydroxyl groups, the polyether containing more than one alkenyl group per molecule. Other monoolefinic monomeric materials may be present in the monomeric mixture if desired, even in predominant proportion. Carboxyvinyl polymers are substantially insoluble in liquid, volatile organic hydrocarbons and are dimensionally stable on exposure to air.

Preferred polyhydric alcohols used to product carboxyvinyl polymers include polyols selected from the class consisting of oligosaccharides, reduced derivatives thereof in which the carbonyl group is converted to an alcohol group, and pentaerythritol; more preferred are oligosaccharides, most preferred is sucrose. It is preferred that the hydroxyl groups of the polyol which are modified be etherified with allyl groups, the polyol having at least two allyl ether groups per polyol molecule. When the polyol is sucrose, it is preferred that the sucrose have at least about five allyl ether groups per sucrose molecule. It is preferred that the polyether of the polyol comprise from about 0.1% to about 4% of the total monomers, more preferably from about 0.2% to about 2.5%.

Preferred monomeric olefinically unsaturated carboxylic acids for use in producing carboxyvinyl polymers used herein include monomeric, polymerizable, alpha-beta monoolefinically unsaturated lower aliphatic carboxylic acids; more preferred are monomeric monoolefinic acrylic acids of the structure

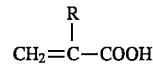

where R is a substituent selected from the group consisting of hydrogen and lower alkyl groups; most preferred is acrylic acid.

Preferred carboxyvinyl polymers used in formulations of the present invention have a molecular weight of at least about 750,000; more preferred are carboxyvinyl polymers having a molecular weight of at least about 1,250,000; most preferred are carboxyvinyl polymers having a molecular weight of at least about 3,000,000.

Other materials can also be used as suspension agents, including those that can impart a gel-like viscosity to the composition, such as water soluble or colloidally water soluble polymers like cellulose ethers (e.g., hydroxyethyl cellulose), guar gum, polyvinyl alcohol, polyvinyl pyrrolidone, hydroxypropyl guar gum, starch and starch derivatives, and other thickeners, viscosity modifiers, gelling agents, etc. Mixtures of these materials can also be used.

The suspending agents, in general, are used at a level of from about 0.1% to about 10%, most commonly from about 0.3% to about 5.0% by weight of the composition.

Optional Components

The compositions herein can contain a variety of non-essential optional components. Such optional ingredients include, for example, preservatives such as benzyl alcohol, methyl paraben, propyl paraben and imidazolidinyl urea; cationic conditioning agents, including both cationic conditioning surfactant and cationic conditioning polymers; fatty alcohols; block polymers of ethylene oxide and propylene oxide such as Pluronic F88 offered by BASF Wyandotte; sodium chloride, sodium sulfate; ammonium zylene sulfonate; propylene glycol; polyvinyl alcohol; ethyl alcohol; Polyquaternium-10 (an industry term designated by The Cosmetic, Toiletry and Fragrance Association (CTFA) for the polymeric quaternary ammonium salt of hydroxyethyl cellulose reacted with trimethyl ammonium substituted eopxide), commercially available from Union Carbide Corp. (Danbury, Conn., U.S.A.) under their UCARE POLYMER JR series of materials, e.g., UCARE POLYMER JR-30M, JR-125 and JR-400; pH adjusting agents such as citric acid, succinic acid, phosphoric acid, sodium hydroxide, sodium carbonate, etc.; perfumes; dyes; and sequestering agents such as disodium ethylenediamine tetraacetate. These optional ingredients are typically used at levels of from about 0.01% to about 10% of the composition. This list of optional ingredients is not meant to be exclusive, and other optional components can be utilized.

Still other optional materials include antidandruff agents such as pyridinethione salts, specifically those in platelet form, as disclosed in U.S. Pat. Nos. 4,379,753 and 4,345,080, incorporated herein by reference. Included, for example, are heavy metal (e.g., zinc), magnesium, and aluminum salts of 1-hydroxy-2-pyridimethione. Other antidandruff agents include selenium compounds such as selenium disulfide. Antidandruff agents are normally used at levels of about 0.1% to about 4% of the composition, preferably about 0.2% to about 2%.

Pediculicides can also be included in the compositions hereof to provide control of lice infestations. Suitable pediculicides are well known in the art and include, for example, pyrethrins such as those disclosed in U.S. Pat. No. 4,668,666, Allan, incorporated herein by reference.

The pH of the present compositions is not generally critical and may be in the range of from 2 to about 10, preferably from about 3 to about 9, more preferably from about 4 to about 8.

METHOD OF MANUFACTURE

The compositions of the present invention, in general, can be made by mixing the materials together at elevated temperature, e.g., about 72° C. The ingredients are mixed thoroughly at the elevated temperature and is then pumped through a high shear mill and then through a heat exchanger to cool it to ambient temperature. The average particle size of the silicone is preferably from about 0.5 to about 20 microns. Alternately, for example, the silicone conditioning agent can be mixed with anionic surfactant and fatty alcohol, such as cetyl and stearyl alcohols, at elevated temperature, to form a premix containing dispersed silicone. The premix can then be added to and mixed with the remaining materials of the shampoo, pumped through a high shear mill, and cooled.

METHOD OF USE

The present compositions are used in a conventional manner for cleaning hair. An effective amount of the composition for cleaning and conditioning hair, typically, from about 1 g to about 20 g of the composition, is applied to hair that has preferably been wetted, generally with water, and then rinsed out. Application to the hair typically includes working the composition through the hair such that most or all of the hair is contacted with the composition.

EXAMPLES

The following Examples further describe and demonstrate the preferred embodiments within the scope of the present invention. The Examples are given solely for the purpose of illustration and are not to be construed as limitations of the present invention as many variations thereof are possible without departing from its spirit and scope. All levels given reflect the active weight of the listed material unless otherwise specifically indicated.

EXAMPLES I–V

The following examples exemplify shampoo compositions of the present invention.

| Component | I | II | III | IV | V |
|---|---|---|---|---|---|
| (ppm or %, by weight, of composition) | | | | | |
| Sodium Laureth-3 Sulfate (%) | 10.00 | 10.00 | 8.60 | 10.00 | 10.00 |
| Cocoamphodiacetate (%)[3] | 3.50 | 3.50 | 3.00 | 3.50 | 3.50 |
| Lauriminodipropionate (%)[4] | 3.50 | 3.50 | 3.00 | 3.50 | 3.50 |
| Cocamidopropyl Hydroxysultaine (%) | | | | 2.70 | |
| PEG-82 Glyceryl Tallowate (%)[5] | 6.00 | 6.00 | 6.00 | 6.00 | 6.00 |
| PEG-30 Glyceryl Cocoate (%)[6] | 4.00 | 4.00 | 4.00 | 4.00 | 4.00 |
| Polyquaternium 10 (%)[1] | | | | 0.10 | 0.05 |
| Ethylene Glycol Distearate (%) | 2.00 | 1.00 | 2.00 | 2.00 | 2.00 |
| Xanthan Gum (%) | 0.10 | 0.10 | | | |
| Dimethicone (%)[2] | 0.40 | 0.40 | 0.30 | 0.40 | 0.40 |
| Perfume (%) | 0.40 | 0.40 | 0.40 | 0.40 | 0.40 |
| Ethylenediamine Tetra-acetic Acid (Na salt) (%) | 0.10 | 0.10 | 0.10 | 0.10 | 0.10 |
| DMDM Hydantoin (%) | 0.20 | 0.20 | 0.20 | 0.20 | 0.20 |
| Citric Acid (%) | 0.25 | 0.25 | 0.25 | 0.25 | 0.25 |

-continued

| Component | I | II | III | IV | V |
|---|---|---|---|---|---|
| Sodium Chloride (ppm) | 184 | 184 | 184 | 184 | 184 |
| SDA #40 Alcohol (ppm) | 150 | 150 | 150 | 150 | 150 |
| Color (ppm) | 8 | 8 | 8 | 8 | 8 |
| DRO Water[7] | | | q.s. to 100% | | |

[1]UCARE Polymer JR-30M, commercially available from Union Carbide Corporation.
[2]A 40/60 blend of SE-76 silicone gum available from GE Silicones and a silicone fluid having a viscosity of about 350 centistokes.
[3]Available under the tradename MIRANOL C-2M from Miranol, Inc.
[4]Available under the tradename DERIPHAT 160C from Henkel, Inc.
[5]Available under the tradename VARONIC LI-48 from Sherex Chemical Company.
[6]Available under the tradename VARONIC LI-63 from Sherex Chemical Company.
[7]Double reverse osmosis water.

The compositions are prepared as follows. A silicone premix is first prepared by adding a portion of the sodium laureth-3 sulfate to the premix tank and heating to 71° C. A portion of the Varonic LI-48 and the sodium chloride are added and allowed to melt. The dimethicone is added and mixed until an emulsion is formed.

The remainder of the sodium laureth-3 sulfate, a portion of the Varonic LI-48, the cocoamphodiacetate, the lauriminopropionate, and the perfume are placed in a separate tank. The mixture (the "main mix") is agitated and heated to 71° C. The ethylene glycol distearate is then added and allowed to melt. The main mix is passed through a high shear mixer and a heat exchanger where it is cooled to 38° C. and collected in a finishing tank. The premix is also sheared, cooled, and collected in the same finishing tank, where the main mix and the premix are mixed until homogeneous. Finally, the remainder of the ingredients are added and mixed into the shampoo composition. The final pH is adjusted by the citric and to within the range of 6.5 to 7.2.

The compositions of the Examples can provide excellent in use hair cleaning and conditioning, along with high silicone hair conditioning agent efficiency.

What is claimed is:

1. A hair conditioning composition comprising;
   (a) from about 5% to about 50% by weight of a detersive surfactant component wherein said detersive surfactant component comprises:
      (i) from about 0.5% to about 20% by weight of the composition of a polyethylene glycol glycerol fatty acid ester nonionic surfactant mixture wherein said mixture comprises polyethylene glycol PEG-82 glyceryl monotallowate and polyethylene glycol PEG-30 glyceryl cocoate; and
      (ii) at least about 2% by weight of the composition, of an anionic surfactant selected from the group consisting of alkyl sulfates, alkyl ethoxylated sulfates, or mixtures thereof;
   (b) from about 0.1% to about 10% by weight, of a dispersed, nonvolatile, insoluble, silicone conditioning agent; and
   (c) water.

2. The composition of claim 1, further comprising a suspending agent for said silicone conditioning agent.

3. The composition of claim 2, wherein said suspending agent is selected from the group consisting of long chain acyl derivatives, long chain amine oxides, xanthan gum, carboxyvinyl polymer suspending agents, and mixtures thereof.

4. The composition of claim 3 wherein said surfactant component further comprises an amphoteric surfactant, a zwitterionic surfactant or a mixture thereof.

5. A shampoo composition as in claim 1, wherein said silicone conditioning agent comprises a mixture of polydimethylsiloxane gum having a viscosity, at 25° C., greater than about 1,000,000 centipoise and polydimethylsiloxane fluid having a viscosity, at 25° C., of from about 10 centipoise to about 100,000 centipoise, said mixture having a gum:fluid weight ratio of from about 30:70 to about 70:30.

6. A shampoo composition as in claim 3, wherein said nonvolatile, silicone fluid component comprises a mixture of polydimethylsiloxane gum having a viscosity, at 25° C., greater than about 1,000,000 centipoise and dimethicone fluid having a viscosity, at 25° C., of from about 10 centipoise to about 100,000 centipoise, said mixture having a gum:fluid weight ratio of from about 30:70 to about 70:30.

7. A shampoo composition according to claim 1, wherein said nonvolatile, silicone fluid component comprises a mixture of polydimethylsiloxane gum having a viscosity, at 25° C., greater than about 1,000,000 centipoise and dimethicone fluid having a viscosity, at 25° C., of from about 10 centipoise to about 100,000 centipoise, said mixture having a gum:fluid weight ratio of from about 40:60 to about 60:40.

8. A shampoo composition according to claim 1, further comprising antidandruff agents selected from the group consisting of pyridinethione salts, selenium compounds, and mixtures thereof.

9. A shampoo composition according to claim 1, wherein the anionic surfactant comprises from about 2% to about 16%, by weight of the composition, of alkyl sulfates and from about 0% to about 14%, by weight of the composition, of ethoxylated alkyl sulfates.

10. A shampoo composition according to claim 9, further comprising from about 1% to about 8%, by weight, of surfactants selected from the group consisting of amphoteric surfactants, zwitterionic surfactants and mixtures thereof; and from about 0.1% to about 10%, by weight, of a suspending agent selected from the group consisting of long chain acyl derivatives, long chain amine oxides, xanthan gum, carboxyvinyl polymer suspending agents and mixtures thereof.

11. A shampoo composition according to claim 1, further comprising from about 0.01% to about 10%, by weight, of polyquaternium-10; and from about 0.1% to about 5%, by weight, of a suspending agent selected from the group consisting of long chain acyl derivatives, long chain amine oxides and mixtures thereof.

* * * * *

UNITED STATES PATENT AND TRADEMARK OFFICE
CERTIFICATE OF CORRECTION

PATENT NO. : 5,612,301

DATED : March 18, 1997

INVENTOR(S) : Everett Junior Inman

It is certified that error appears in the above-indentified patent and that said Letters Patent is hereby corrected as shown below:

At column 9, line 36 "al iphatic" should read --aliphatic--.

At column 9, line 47 "aspattic" should read --aspartic--.

At column 9, line 58 "cocoamidodimethylpropyl sultaine" should read --cocoamidodimethylpropylsultaine--.

At column 9, line 59 "stearyl amidododimethylpropylsultaine" should read --stearylamidododimethylpropylsultaine--.

At column 10, lines 59-60 "n-alkyl iminodipropionates" should read --n-alkyliminodipropionates--.

At column 11, line 65 ".polypropylene" should read --polypropylene--.

At column 14, line 3 "Theft" should read --Their--.

Signed and Sealed this

Twenty-sixth Day of August, 1997

Attest:

BRUCE LEHMAN

Attesting Officer

Commissioner of Patents and Trademarks